US006731974B2

(12) United States Patent
Levitan et al.

(10) Patent No.: US 6,731,974 B2
(45) Date of Patent: May 4, 2004

(54) METHOD AND SYSTEM FOR MEASURING HEART RATE VARIABILITY

(75) Inventors: Jacob Levitan, Herzliya Pituach (IL); Meir Lewkowicz, Elon Moreh (IL)

(73) Assignee: LEV-EL Diagnostics of Heart Disease Ltd., Ariel (IL)

( * ) Notice: Subject to any disclaimer, the term of this patent is extended or adjusted under 35 U.S.C. 154(b) by 569 days.

(21) Appl. No.: 09/760,594

(22) Filed: Jan. 16, 2001

(65) Prior Publication Data

US 2001/0008954 A1 Jul. 19, 2001

(30) Foreign Application Priority Data

Jan. 19, 2000 (IL) .................................. 134123

(51) Int. Cl.[7] .......................................... A61B 5/0468
(52) U.S. Cl. ...................................... 600/515; 600/523
(58) Field of Search ................................. 600/481, 508, 600/509, 515, 516, 517, 518, 523

(56) References Cited

U.S. PATENT DOCUMENTS

| | | | | |
|---|---|---|---|---|
| 4,018,219 A | * | 4/1977 | Hojaiban | 600/519 |
| 5,201,321 A | * | 4/1993 | Fulton | 600/515 |
| 5,333,615 A | * | 8/1994 | Craelius et al. | 600/509 |
| 5,560,368 A | * | 10/1996 | Berger | 600/517 |
| 5,682,901 A | | 11/1997 | Kamen | |
| 5,755,671 A | * | 5/1998 | Albrecht et al. | 600/516 |
| 5,769,793 A | * | 6/1998 | Pincus et al. | 600/515 |
| 6,144,878 A | * | 11/2000 | Schroeppel et al. | 600/515 |

FOREIGN PATENT DOCUMENTS

DE 43 20 519 A1 6/1993

OTHER PUBLICATIONS

Marciano et. al. "Quantification of Poincare' Maps for the Evaluation of Heart Rate Variability", Computers in Cardiology, IEEE, pp. 577–580, 1994.
Hnatkova K., "Numeric Processing of Lorenz Plots of R–R Intervals From Long–term ECGs", Journal of Cardiology, vol. 28 Supplement, pp. 74–80, 1995.

* cited by examiner

*Primary Examiner*—Willis R. Wolfe
(74) *Attorney, Agent, or Firm*—Edward Langer; Shiboleth, Yisraeli, Roberts, Zisman & Co.

(57) ABSTRACT

A system for measuring heart rate variability (HRV) of a patent comprises:

recording means for obtaining and regulating heartbeat-to-heartbeat intervals for a predetermined period of time;

processing means for digitizing said intervals, forming a recurrence plot, and assigning a unit mass to each point on the plot representing a measured interval, and calculating the determinant by the expression $$Q_{det} = Q_{xx} Q_{yy}$$

wherein:

$Q_{xx}$ is the quadrupole moment relative to the X axis of the principal coordinate, $Q_{yy}$ is the quadrupole moment relative to the Y axis of the principal coordinate; and $Q_{det}$ is the product of $Q_{xx}$ and $Q_{yy}$.

11 Claims, 3 Drawing Sheets

METHOD AND SYSTEM FOR MEASURING HEART RATE VARIABILITY

FIELD OF THE INVENTION

The present invention relates to a method and a system for measuring heart rate variability (HRV).

BACKGROUND OF THE INVENTION

The study of HRV has been in use for many years as part of clinical, prognostic work; there are international guidelines for evaluating conventional HRV parameters. The conventional parameters are partly frequency domain parameters (power spectra), and partly time domain parameters (various RMS estimates). These methods, though in general successful, are not always conclusive.

Over the last few years, new methods of analyzing R—R intervals of PQRS plots representative of the human heartbeat wave have appeared, all of them showing improved diagnostic and prognostic performance. It has been shown that so-called scale dependent methods outperform scale-independent measure with respect to separating healthy subjects from patients suffering from certain cardiac dysfunctions. But in clinical practice, it is of interest to examine whether, within a group of heart patients, one can extract a subgroup of patents who are at risk, e.g., with respect to sudden cardiac death, rather than to verify the presumably known fact that they do not belong to a group of healthy subjects. It has been shown that, while scale-dependent methods worked in the former case, one had to use scale-independent measures in the latter case.

In practical medicine, recurrence plots of the R—R intervals are used for diagnostic purposes by visual inspection. Since the density of the points is ignored in a visual presentation of the plot, sometimes similar patterns are found for recordings with different HRV's. Although some attempts have been made to include the density of points, this procedure is performed manually and is thus dependent on the performer's skins. Hence, crucial information about the topology of the recurrence plot might be lost.

FIG. 1 illustrates an ECO signal wave. The electrophysiological features of the heart are generally measured by an electrocardiograph, and the electro-physiological recording of the heart function is known as the ECG or EKG. The six features P, Q, R, S, T, U (FIG. 1) describe the sequence of two cycles wherein the R potential is the highest peak. It is therefore easy to distinguish the other five features and the R-peak of the next sequence. The R—R distance is measured in milliseconds and represents the inverse heart rate (HR). The HR is normally not constant, but continually oscillates around its mean level. These short-term cyclic changes are primarily caused by cardiac autonomic modulation.

The calculation of HR and its variability can be used to estimate autonomic activity as and in particular, to evaluate autonomic nervous system influences on heart functions. The autonomic nervous system (ANS) comprises all of the efferent nerves through the visceral organs, including the cardiovascular system, the and the peripheral involuntary muscles. The ANS is generally described as a combination of two main systems that balances and interacts; the sympathetic, regulated by adrenergic activities, and the parasympathetic, cholinergically regulated. One of the main nerves controlling the activity of the heart is the fast-acting, parasympathetic Vagus nerve.

It is generally accepted today that HRV measurement is also a valuable took for the determination of the status of the ANS. Changes in vagal activity cause immediate large changes in instantaneous HR, whereas changes in sympathetic activities are associated with more gradual, slow changes.

The measurement of HR and its rhythmicity, HRV, are only used as a diagnostic tool in cardiology. A stable heart rate is a sign that the heart does not respond to external influences, which responses are mainly regulated by the ANS. Such a situation is dangerous for the individual and is considered to be a pathological symptom. Research has indicated that a quantification of HRV, the discrete beat-to-beat variability in the heart, plays an important prognostic role as an indicator of risk associated with a large variety of diseases, behavioral disorders, mortality and also aging, independent of other risk factors.

Depressed, low HRV has been shown to be a powerful predictor of cardiac events after myocardial infarct. It is therefore crucial to establish a measure of HRV and to quantitatively classify the HRVs of different pathological cases, in order to discriminate between healthy HR profiles and those of patients at risk.

The commercially available medical device for detection of HVR is the Holter 24-hour recording and analysis instrument. A Holter instrument monitor continuously records heart patterns from electrodes attached to the patient for a 24-hour period. The Holter recording technique records the ECG on analog magnetic tape, and a Holter scanner analyzes the tape 60 or 120 times to produce a final report. A Holter scanner report may contain statistical calculations of the heart activity and a detailed report of abnormal cardiological events, such as sinus pauses and propped beats. A limited factor of this technology is the long, 24-hour measurement time and the lack of a graphic print-out summarizing the entire examination period as well as a material evaluation of the total measurement.

U.S. Pat. No. 5,682,901 (Kamen) discloses a method and apparatus for measuring autonomic activity of a patient during a short duration. The method utilizes a visual description of the recurrence plot and separates between direct pathological states, according to different patterns. The method, however, suffers from the fact that the figures of the recurrence plots do not allow the inspection of the density of the data points, which varies over the whole contour, but only renders information of the general shape of the plot. The method and apparatus of Kamen include performing a calculation of the correlation dimension in order to quantify the degree of heart failure, but such a calculation necessitates a dimension that is partly bases on a visual, subjective inspection. Such a visual inspection is known to be unreliable.

SUMMARY AND OBJECTS OF THE INVENTION

It is therefore a broad object of the present invention to provide an accurate method and system for measuring HRV over a relatively short period of time of 60 minutes or less.

It is a further object of the present invention to provide a method and a system for measuring HRV, giving results which are more precise and easier to evaluate.

It is a still object of tie present invention to provide a method and system enabling a prognosis of the status of a patient with a history of heart failure or impaired heart function, by quantification of the degree of heart failure or heart function impairment.

It is a yet further object of the present invention to provide a method and a system allowing for the classification of patients with a history of heart failure or impaired heart function into the following three groups, ordered according to the risk of death due to heart failure: (1) patients with a minimal risk of sudden death, comparable to that of healthy individuals; (2) patients with an increased risk of sudden death, and (3) patients with a high risk of sudden death.

In accordance with the present invention, there is therefore provided a system for measuring heart rate variability (HRV) of a patient, comprising recording means for obtaining and recording heartbeat-to-heartbeat intervals for a predetermined period of time; process means for digitizing said intervals, forming a recurrence plot, and assigning a unit mass to each point on the plot representing a measured interval, and calculating the determinant by the expression $$Q_{det} = Q_{xx} Q_{yy}$$

wherein:

$Q_{xx}$ is the quadrople moment relative to the X axis of the principal coordinate, $Q_{yy}$ is the quadrople moment relative to the Y axis of the principal coordinate; and $Q_{det}$ is the product to $Q_{xx}$ and $Q_{yy}$.

The invention further provides a method for measuring the heart rate variability (HRV) of a patient, comprising collecting data of heartbeat-to-heartbeat intervals; determining the intervals during a predetermined period of time; generating a recurrence plot from said determined intervals, and calculating the determinant by the expression $$Q_{det} = Q_{xx} Q_{yy}$$

wherein:

$Q_{xx}$ is the quadrupole moment relative to the X axis of the principal coordinate, $Q_{yy}$ is the quadrupole moment relative to the X axis of the principal coordinate; and $Q_{det}$ is the product of $Q_{xx}$ and $Q_{yy}$,

BRIEF DESCRIPTION OF THE DRAWINGS

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of like preferred embodiments of the present invention only, and are presented in the cause of providing what is believed to be the most useful and readily understood description of the principles and conceptual aspect of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is an illustration of a conventional electrocardiograph measurement;

FIG. 2 is a block diagram of the system accord to the present invention for measuring HRV;

FIG. 3 illustrates a recurrence or Poincaré plot;

FIG. 4 is a block diagram of the method of the present invention for measuring HRV; and FIGS. 5A–5C are recurrence plots indicative of patients with various degrees of risk due to heart failure.

DETAILED DESCRIPTION OF THE EXEMPLARY EMBODIMENTS

Figure 1:
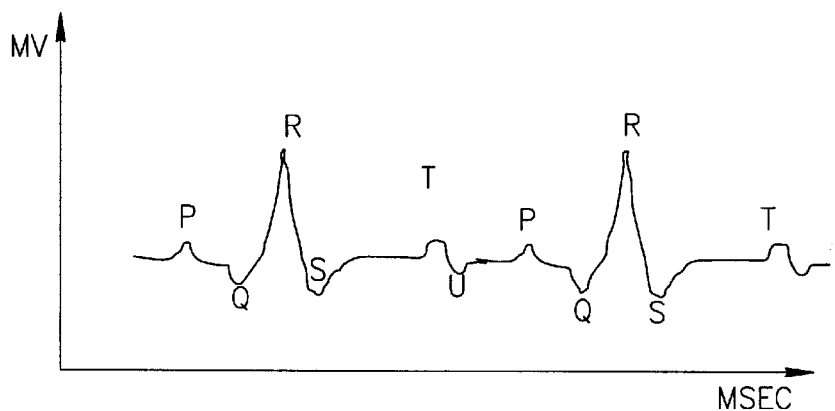
Figure 2:
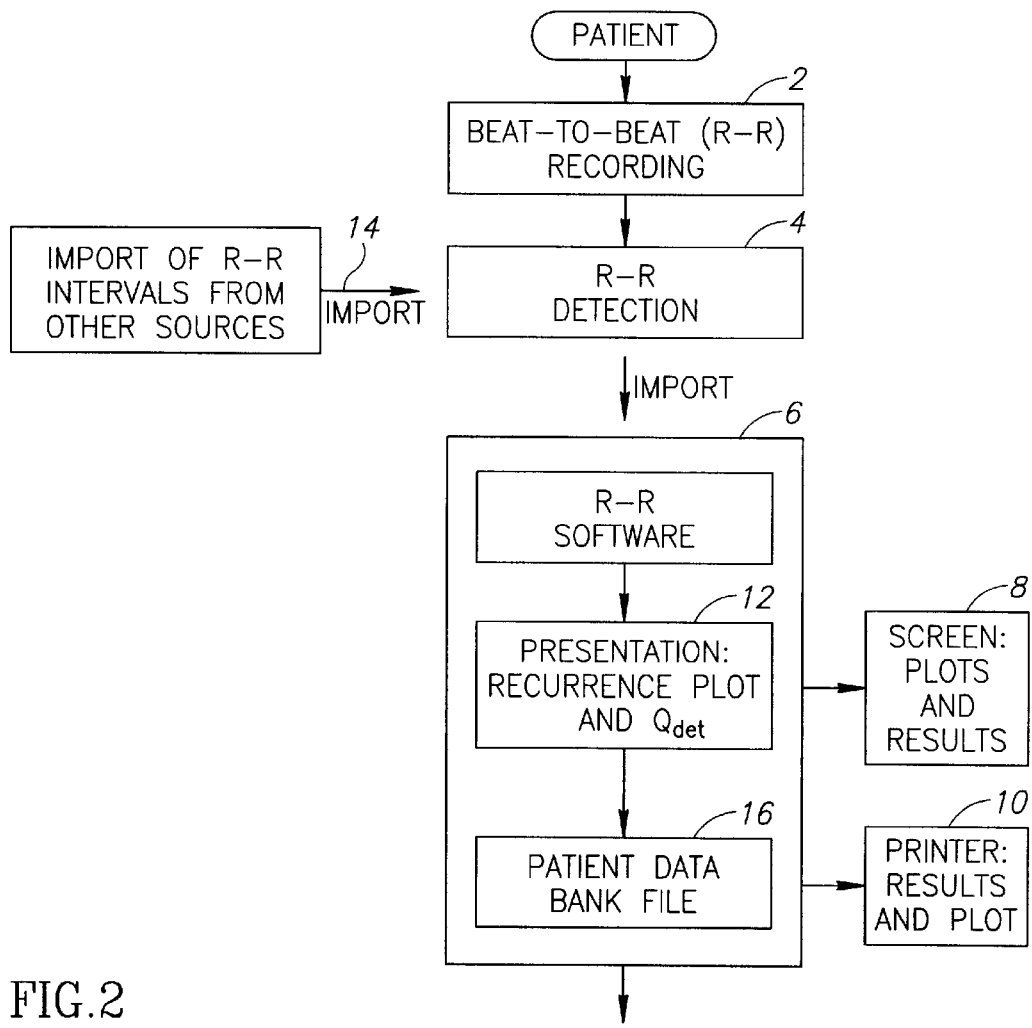

The system of measuring HRV according to the present invention will now be described with reference to FIG. 2.

The patient is placed in a resting position on a table and electrodes attached to the patient are connected to a recorder 2, either by wires or by means of wireless technology. Any instruments that can measure and record the R—R distance with the sensitivity and accuracy of 1 msec can be applied, such as, for example, a conventional ECG apparatus, a Holter 24-hour recorder, or a specifically designed instrument. The recording is made for a predetermined period of time, from 15 minutes to 24 hours.

The recorded R—R intervals can then be obtained from an ECG by a PQRS detector 4, or from a specific dedicated recorder, and are transferred to a processing system 6, which may be a personal computer equipped with a software program which detects the R peaks, calculates the R—R intervals between adjacent peek in msec, and processes the data obtained. Optionally, detector 4 may also include terminal 14 for inputting R—R intervals from other sources, and a patient data bank file 16 for fixture use. The plots and calculations, together with clinical and personal data regarding the patient, will be presented on a screen 8; a printer 10 can provide a printout.

Figure 3:
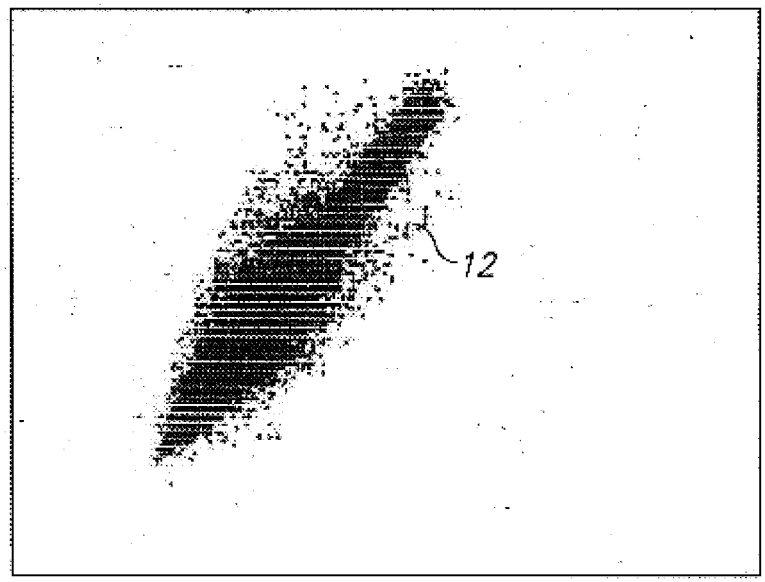

The R—R interval data is plotted in a two- or three-dimensional recurrence or Poincaré plot 12 (FIG. 3), as an illustration of the HRV. By using a specific mathematical procedure called the Quadrupole Moment Method (QMM) as will be described below, a certain index or value $Q_{det}$, a quantitative measure for the HRV, is calculated.

Figure 4:
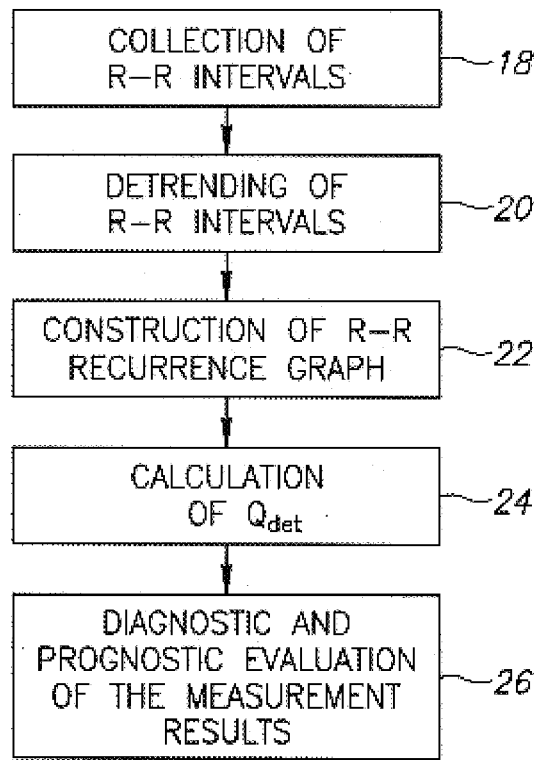

Referring now to FIG. 4, the method according to the present invention will be described.

The patient's ECG is collected, recorded by the recorder 2 and digitized at 18. From the digitized ECG, the R—R intervals are measured and arranged in a two-dimensional array, e.g., in columns, where one column is the number of the interval, represented by the integers 1, 2, 3 ..., and the second column is the R—R interval expressed in msec, typically between 500–1500 msec for each R—R interval. The detrending is achieved by calculating the local average value of the R—R time series in a running window, typically of the length $2^m$, where m is a positive interger. This average value is subtracted from the R—R series at the center position of the running window; resulting in the locally determined R—R interval time series.

The fist R—R interval, together with the second R—R interval is marked as a point on a two-dimensional coordinate system 20, wherein the X coordinate is the first R—R interval and the Y coordinate is the second interval. The second interval is hereafter marked as the next X coordinate and the consecutive interval as the next Y-coordinate. This procedure is continued, the Y coordinate being partly switched to an X-coordinate in the following point. The procedure starts from the first number in the file and obviously ends with the last. This procedure is termed "detrending," meaning that every deviation in the heart rate variability is measured relative to an overall average and there is no due consideration given to short term local fluctuations that are not caused by internal variables of the heart rhythm, but are enforced by external conditions. Detrending becomes especially crucial in measurements over an extended period of time, e.g., 24 hours, and in every measurement where the patients measured are left in uncontrolled conditions. The importance of detrending resides in the accuracy of both prognosis and diagnosis, which depend thereon.

The evolving recurrence plot 22 of scattered points in FIG. 4 exhibits the density of the points. Each data point in the recurrence plot 12 (FIG. 3) is assigned a unit mass. The two-dimensional body is then analyzed in terms of a gravitational, multi-pole expansion $\Phi$:
wherein:

$$\phi = \int \frac{\rho(\vec{r}')}{|\vec{r} - \vec{r}'|} d^2\vec{r}' \approx \frac{M}{r} + \frac{\overline{R}_{cm} \cdot \overline{r}}{r^3} + \frac{1}{2}\sum Q_{ij} \frac{x_i x_j}{r^5} + \ldots \quad (1)$$

$\rho(r')$ is the density of mass (here equal to 1) at the point (r');
$\bar{r}$ is the position vector of the observation point;
$\bar{r}'$ is the position vector of the mass at r';
$d^2\bar{r}'$ is an infinitesimal area around r';
M is a number of masses;
$\overline{R}_{cm} = \int \vec{r}' d^2\vec{r}' = 0$
   is the dipole moment;
$Q_{ij}$ is the normalized quadrupole moment:

$$Q_{ij} = \frac{1}{M} \sum_{masses} (3x_i' x_j' - r'^2 \delta_{ij}) \quad (2)$$

$x_i$ is the X or Y coordinate of the vector $\bar{r}_i$; and
$x_i x_j$ is the product of two such coordinates.
For the principal axis:

$$Q_{ij} = \begin{pmatrix} Q_{xx} & 0 \\ 0 & Q_{yy} \end{pmatrix} \Rightarrow$$

geometrical description by $Q_{det} \equiv Q_{xx} \cdot Q_{yy}$.

The first term in equation (1) is the monopole, and represents the number of data points, which is irrelevant to the analysis of the HRV. The second term is the gravitational dipole moment and vanishes by choosing the origin of the coordinate system in the center of the mass. The first significant term is hence the third term in the equation (1), the quadrupole moment. This moment is expressed as a 2×2 matrix and is rendered independent of the number of data points by dividing it by the number of data points. By diagonalization, the off-diagonal elements of this matrix are set equal to zero. This procedure defines, in fact, a new coordinate axis, the Principal Axis. The two non-vanishing terms are symbolized by $Q_{xx}$ and $Q_{yy}$. The expressions are given in equation (2).

Finally, the determinant of the matrix $Q_{det} = Q_{xx} \cdot Q_{yy}$ is calculated at 24. This determinant is one of the parameters which can be used in the further investigation of the state of the heart of the patient whose ECG has been measured.

In certain cases, as with different-shaped reoccurrence plots for different detrending scales, the multipole expansion has to be continued.

More comparative parameters are extracted from a higher dimensional recurrence plot, i.e., for n's dimension, the recurrence plot is constructed from the n's dimensional vector, $R-R_i, R-R_{i+1}, R-R_{i+2}, \ldots R-R_{i+n}$. Here, the multipole expansion is performed on the solution of the Laplace Equation in n dimensions.

Figure 5A:
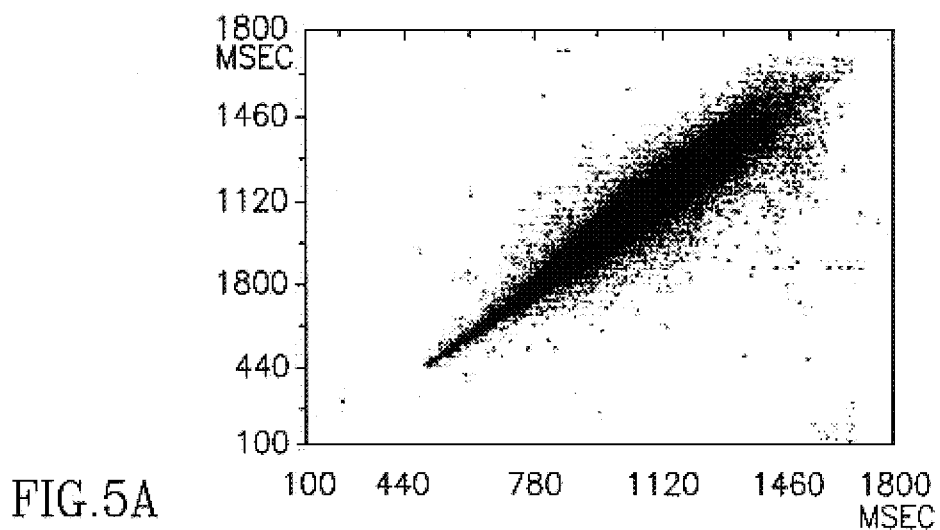
Figure 5B:
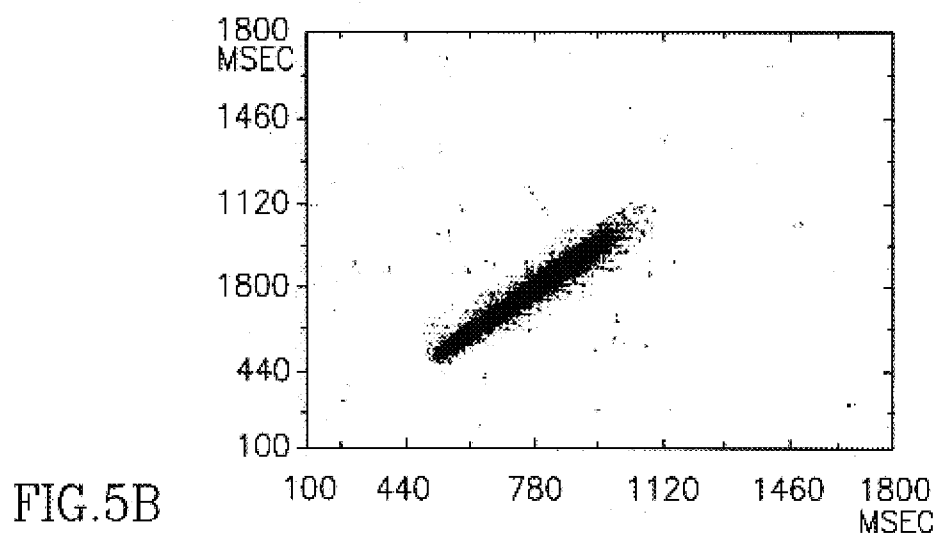
Figure 5C:
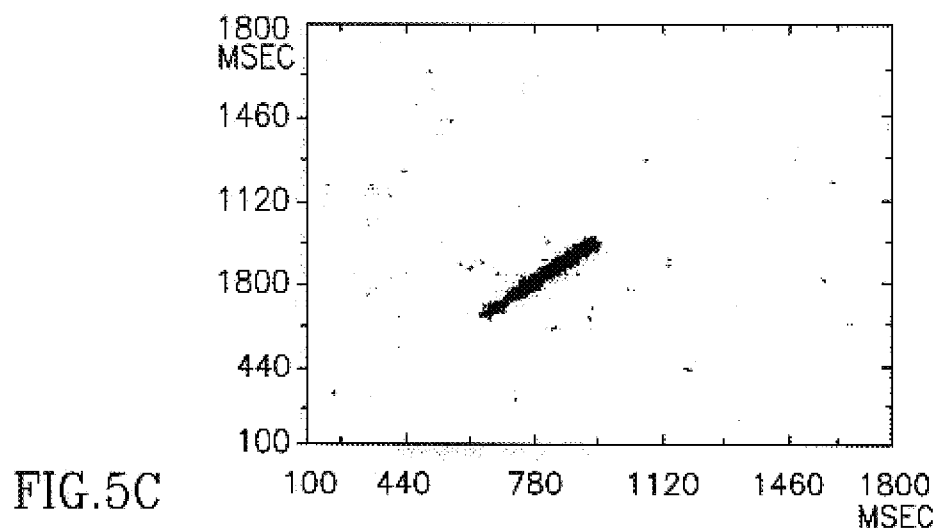

Eventually, diagnostic and prognostic evaluation is performed at 26, on the basis of the measurement results. For example, as seen in FIGS. 5A to 5C, a patient with a minimal risk of sudden death, comparable to that of a healthy individual, will have a recurrence plot as shown in FIG. 5A; a patient with an increased risk will have a recurrence plot as shown in FIG. 5B, and a patient with a high risk will have a recurrence plot as shown in FIG. 5C.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A system for measuring heart rate variability (HRV) of a patient, said system comprising:

recording means for obtaining and recording heartbeat-to-heartbeat intervals for a predetermined period of time;

processing means for digitizing said intervals, forming a recurrence plot, and assigning a unit mass to each point on the plot representing a measured interval, and calculating the determinant by the expression $$Q_{det} = Q_{xx} Q_{yy}$$

wherein:

$Q_{xx}$ is the quadrupole moment relative to the X axis of the principal coordinate, $Q_{yy}$ is the quadrupole moment relative to the Y axis of the principal coordinate; and $Q_{det}$ is the product of $Q_{xx}$ and $Q_{yy}$.

2. The system as claimed in claim 1, wherein said recording means further comprises an input terminal for inputting data concerning heartbeat—heartbeat intervals obtained from other sources.

3. The system as claimed in claim 1, wherein said recurrence plot is formed on a screen.

4. The system as claimed in claim 1, wherein said recurrence plot is produced by a printer.

5. The system as claimed in claim 1, further comprising a patient data bank file for future use.

6. A method for measuring the heat rate variability (HRV) of a patient, said method comprising:

collecting data of heartbeat-to-heartbeat intervals;

determining the intervals during a predetermined period of time;

generating a recurrence plot from said determined intervals, and calculating the determinant by the expression $$Q_{det} = Q_{xx} Q_{yy}$$

wherein:

$Q_{xx}$ is the quadrupole moment relative to the X axis of the principal coordinate, $Q_{yy}$ is the quadrupole moment relative to the Y axis of the principal coordinate; and $Q_{det}$ is the product of $Q_{xx}$ and $Q_{yy}$.

7. The method as claimed in claim 6, further comprising digitizing said intervals prior to generating a reoccurrence plot.

8. The method as claimed in claim 6, further comprising exhibiting said recurrence plot on a screen.

9. The method as claimed in claim 6, further comprising printing said recurrence plot.

10. The method as claimed in claim 6, evaluating the state of the patient's sympathetic and parasympathetic nervous system, based on the HRV measurements obtained.

11. The method as claimed in claim 6, further comprising transferring the HRV measurements and calculated determinant to a patient data bank file.

* * * * *